United States Patent
Marsh et al.

(10) Patent No.: US 10,555,600 B2
(45) Date of Patent: Feb. 11, 2020

(54) CLEANING APPLIANCE

(71) Applicant: Dyson Technology Limited, Wiltshire (GB)

(72) Inventors: Jonathan George Marsh, Swindon (GB); Thomas Douglas Ridley, Bristol (GB); Sammantha Stephanie Harris, Swindon (GB); Boris Zukina, Bristol (GB); Christopher Daniel Currer Wilkinson, Swindon (GB)

(73) Assignee: Dyson Technology Limited, Malmesbury, Wiltshire (GB)

( * ) Notice: Subject to any disclaimer, the term of this patent is extended or adjusted under 35 U.S.C. 154(b) by 37 days.

(21) Appl. No.: 15/793,498

(22) Filed: Oct. 25, 2017

(65) Prior Publication Data

US 2018/0110322 A1    Apr. 26, 2018

(30) Foreign Application Priority Data

Oct. 26, 2016 (GB) .................................. 1618075.4

(51) Int. Cl.
| | |
|---|---|
| *A46B 15/00* | (2006.01) |
| *A61C 17/22* | (2006.01) |
| *G02B 5/08* | (2006.01) |
| *G02B 1/14* | (2015.01) |
| *G02B 27/14* | (2006.01) |

(Continued)

(52) U.S. Cl.
CPC ...... *A46B 15/0022* (2013.01); *A46B 15/0004* (2013.01); *A46B 15/0036* (2013.01); *A46B 15/0044* (2013.01); *A61C 17/221* (2013.01); *A61C 17/222* (2013.01); *A61C 17/225* (2013.01); *A61C 17/227* (2013.01); *G02B 1/14* (2015.01); *G02B 5/0808* (2013.01); *G02B 27/144* (2013.01); *A46B 2200/1066* (2013.01); *A61C 17/28* (2013.01); *A61C 17/36* (2013.01)

(58) Field of Classification Search
CPC ............ A46B 15/0004; A46B 15/0022; A46B 15/0036; A46B 15/0044; A61C 17/221; A61C 17/222; A61C 17/225; A61C 17/227
See application file for complete search history.

(56) References Cited

U.S. PATENT DOCUMENTS

| | | |
|---|---|---|
| 2,766,472 A | 10/1956 | Durrett |
| 3,195,537 A | 7/1965 | Blasi |
| (Continued) | | |

FOREIGN PATENT DOCUMENTS

| | | |
|---|---|---|
| CA | 2 762 842 | 11/2010 |
| CN | 2580827 | 10/2003 |
| (Continued) | | |

OTHER PUBLICATIONS

Search Report dated Mar. 21, 2017, directed to GB Application No. 1618075.4; 2 pages.

(Continued)

*Primary Examiner* — Randall E Chin
(74) *Attorney, Agent, or Firm* — Morrison & Foerster LLP (57) ABSTRACT

A dental cleaning appliance includes a handle; an electronic display, and a control circuit for activating the display. The handle includes a body and a transparent panel connected to the body. The panel defines a trough-shaped recess beneath which the display is located.

28 Claims, 9 Drawing Sheets

(51) Int. Cl.
    *A61C 17/28* (2006.01)
    *A61C 17/36* (2006.01)

(56) References Cited

U.S. PATENT DOCUMENTS

| | | | |
|---|---|---|---|
| 3,235,897 A | 2/1966 | Fortenberry | |
| 3,667,454 A | 6/1972 | Prince | |
| 4,315,741 A | 2/1982 | Reichl | |
| 4,779,173 A | 10/1988 | Carr et al. | |
| 4,845,796 A | 7/1989 | Mosley | |
| 4,961,698 A | 10/1990 | Vlock | |
| 4,978,297 A | 12/1990 | Vlock | |
| 5,115,533 A * | 5/1992 | Hukuba | A46B 15/0002 15/105 |
| 5,218,956 A | 6/1993 | Handler et al. | |
| 5,339,479 A | 8/1994 | Lyman | |
| 5,372,501 A | 12/1994 | Shalvi | |
| 5,393,153 A | 2/1995 | Bouthillier et al. | |
| 5,561,881 A | 10/1996 | Klinger et al. | |
| 5,673,451 A | 10/1997 | Moore et al. | |
| 5,704,087 A | 1/1998 | Strub | |
| 5,784,742 A | 7/1998 | Giuliani et al. | |
| 5,815,872 A | 10/1998 | Meginniss, III et al. | |
| 5,876,207 A | 3/1999 | Sundius et al. | |
| 5,918,995 A | 7/1999 | Puurunen | |
| 6,026,828 A | 2/2000 | Altshuler | |
| 6,029,304 A | 2/2000 | Hulke et al. | |
| 6,047,429 A | 4/2000 | Wu | |
| 6,155,824 A | 12/2000 | Kamen et al. | |
| 6,164,967 A | 12/2000 | Sale et al. | |
| 6,202,242 B1 | 3/2001 | Salmon et al. | |
| 6,402,410 B1 | 6/2002 | Hall et al. | |
| 6,536,979 B1 | 3/2003 | Kenny et al. | |
| 6,599,126 B1 | 7/2003 | Sale et al. | |
| 6,606,755 B1 | 8/2003 | Robinson et al. | |
| 6,689,078 B1 | 2/2004 | Rehkemper et al. | |
| 6,739,782 B1 | 5/2004 | Rehkemper et al. | |
| 6,766,549 B2 | 7/2004 | Klupt | |
| 7,080,980 B2 | 7/2006 | Klupt | |
| 7,596,827 B1 | 10/2009 | Puneet | |
| 7,896,567 B2 | 3/2011 | Burrowes | |
| 8,287,203 B2 | 10/2012 | Gruber et al. | |
| 8,430,590 B2 | 4/2013 | Boland et al. | |
| 8,522,384 B2 | 9/2013 | Leung | |
| 8,651,340 B2 | 2/2014 | Lelieveld et al. | |
| 8,904,590 B2 | 12/2014 | Jungnickel | |
| 9,144,298 B2 | 9/2015 | Fattori | |
| 2002/0004817 A1 | 4/2002 | Hall et al. | |
| 2002/0044817 A1 | 4/2002 | Hall et al. | |
| 2002/0100134 A1 | 8/2002 | Dunn et al. | |
| 2002/0129454 A1 | 9/2002 | Hilscher et al. | |
| 2002/0133308 A1 | 9/2002 | Lundell et al. | |
| 2002/0152565 A1 | 10/2002 | Klupt | |
| 2003/0056307 A1 | 3/2003 | Tybinkowski et al. | |
| 2003/0131427 A1 | 7/2003 | Hilscher et al. | |
| 2003/0205492 A1 | 11/2003 | Ferber et al. | |
| 2004/0060138 A1 | 4/2004 | Pfenniger et al. | |
| 2004/0143920 A1 | 7/2004 | Nanda | |
| 2005/0004498 A1 | 1/2005 | Klupt | |
| 2005/0034256 A1 | 2/2005 | Kemp et al. | |
| 2005/0050658 A1 | 3/2005 | Chan et al. | |
| 2005/0104556 A1 | 5/2005 | Pfenniger et al. | |
| 2005/0238412 A1 | 10/2005 | Jacobs et al. | |
| 2005/0254992 A1 | 11/2005 | Jenkins et al. | |
| 2005/0271997 A1 | 12/2005 | Mikami et al. | |
| 2006/0037158 A1 | 2/2006 | Foley et al. | |
| 2006/0130253 A1 | 6/2006 | Rycroft | |
| 2006/0292521 A1 | 12/2006 | Hegemann | |
| 2007/0039109 A1 | 2/2007 | Nanda | |
| 2007/0041779 A1 | 2/2007 | Kuo | |
| 2007/0080240 A1 | 4/2007 | Schuetz | |
| 2007/0094822 A1 | 5/2007 | Gatzerneyer et al. | |
| 2007/0190509 A1 | 8/2007 | Kim | |
| 2008/0008979 A1 | 1/2008 | Thomas et al. | |
| 2008/0060148 A1 | 3/2008 | Pinyayev et al. | |
| 2008/0109973 A1 | 5/2008 | Farrell et al. | |
| 2008/0141476 A1 | 6/2008 | Gatzemeyer et al. | |
| 2008/0196185 A1 | 8/2008 | Gatzemeyer et al. | |
| 2008/0250591 A1 | 10/2008 | Nanda | |
| 2008/0313829 A1 | 12/2008 | Dabrowski | |
| 2009/0064429 A1 | 3/2009 | Hall et al. | |
| 2009/0064430 A1 | 3/2009 | Jimenez et al. | |
| 2009/0136285 A1 | 5/2009 | Hall et al. | |
| 2009/0144919 A1 | 6/2009 | Nanda | |
| 2009/0148808 A1 | 6/2009 | Alexander et al. | |
| 2009/0183689 A1 | 7/2009 | Moore et al. | |
| 2009/0291422 A1 | 11/2009 | Puurunen et al. | |
| 2009/0305187 A1 | 12/2009 | Janssen et al. | |
| 2009/0307859 A1 | 12/2009 | Mottram et al. | |
| 2009/0313778 A1 | 12/2009 | Wong et al. | |
| 2010/0223742 A1 | 9/2010 | Kang | |
| 2010/0269276 A1 | 10/2010 | Faranda et al. | |
| 2010/0281636 A1 | 11/2010 | Ortins et al. | |
| 2010/0325828 A1 | 12/2010 | Braun et al. | |
| 2011/0010876 A1 | 1/2011 | Iwahori et al. | |
| 2011/0027749 A1 | 2/2011 | Syed | |
| 2011/0056033 A1 | 3/2011 | Iwahori et al. | |
| 2011/0146015 A1 | 6/2011 | Moskovich et al. | |
| 2011/0146016 A1 | 6/2011 | Gatzemeyer et al. | |
| 2011/0184427 A1 | 7/2011 | Mcclure | |
| 2011/0247158 A1 | 10/2011 | Jungnickel et al. | |
| 2011/0275424 A1 | 11/2011 | Schmid et al. | |
| 2011/0314677 A1 | 12/2011 | Meier et al. | |
| 2012/0066848 A1 | 3/2012 | Klemm et al. | |
| 2012/0110763 A1 | 5/2012 | Jungnickel et al. | |
| 2012/0137454 A1 | 6/2012 | Huy et al. | |
| 2012/0183926 A1 | 7/2012 | Shalev | |
| 2012/0266396 A1 | 10/2012 | Leung | |
| 2013/0045457 A1 | 2/2013 | Chettiar | |
| 2013/0122453 A1 | 5/2013 | Paxton et al. | |
| 2013/0125327 A1 | 5/2013 | Schmid et al. | |
| 2013/0174366 A1 | 7/2013 | Stebila et al. | |
| 2013/0177863 A1 | 7/2013 | Shreve | |
| 2013/0205528 A1 | 8/2013 | Jungnickel et al. | |
| 2013/0311321 A1 | 11/2013 | Gatzemeyer et al. | |
| 2014/0007361 A1 | 1/2014 | Nazaroff et al. | |
| 2014/0033034 A1 | 1/2014 | Patel | |
| 2014/0096332 A1 | 4/2014 | Kitagawa et al. | |
| 2014/0123420 A1 | 5/2014 | Nanda | |
| 2014/0134568 A1 | 5/2014 | Heinrich et al. | |
| 2014/0259474 A1 | 9/2014 | Sokol et al. | |
| 2014/0304932 A1 | 10/2014 | Patel | |
| 2014/0315142 A1 * | 10/2014 | Montgomery | A61C 19/066 433/29 |
| 2014/0332028 A1 | 11/2014 | Tran | |
| 2015/0013088 A1 | 1/2015 | Li | |
| 2015/0044629 A1 * | 2/2015 | Wang | A46B 15/0006 433/27 |
| 2015/0230899 A1 | 8/2015 | Vetter et al. | |
| 2015/0313353 A1 | 11/2015 | Schmalhurst et al. | |
| 2015/0335144 A1 | 11/2015 | Patel | |
| 2015/0335145 A1 | 11/2015 | Bloch et al. | |
| 2015/0342337 A1 | 12/2015 | Bloch | |
| 2016/0045020 A1 | 2/2016 | Belge-Barnes | |
| 2016/0081465 A1 | 3/2016 | Metter | |
| 2016/0296003 A1 | 10/2016 | Beckerman et al. | |
| 2016/0324595 A1 | 11/2016 | Benning | |
| 2016/0331114 A1 | 11/2016 | Follows et al. | |
| 2016/0331115 A1 | 11/2016 | Follows et al. | |
| 2016/0331116 A1 | 11/2016 | Follows et al. | |
| 2016/0331498 A1 | 11/2016 | Follows et al. | |
| 2017/0056142 A1 | 3/2017 | Baragona et al. | |
| 2017/0318951 A1 | 11/2017 | Taghvai | |
| 2018/0028296 A1 | 2/2018 | Lee | |
| 2018/0055212 A1 | 3/2018 | Follows et al. | |
| 2018/0078350 A1 | 3/2018 | Zachar et al. | |
| 2018/0110601 A1 | 4/2018 | Mighall et al. | |
| 2019/0082819 A1 | 3/2019 | Katano et al. | |

FOREIGN PATENT DOCUMENTS

| | | |
|---|---|---|
| CN | 101683288 | 3/2010 |
| CN | 201668525 | 12/2010 |
| CN | 202020561 | 11/2011 |

(56) References Cited

FOREIGN PATENT DOCUMENTS

| | | |
|---|---|---|
| CN | 202143656 | 2/2012 |
| CN | 202526334 | 11/2012 |
| CN | 102846393 | 1/2013 |
| CN | 103347417 | 10/2013 |
| CN | 103783811 | 5/2014 |
| CN | 104523345 | 4/2015 |
| CN | 204411007 | 6/2015 |
| CN | 204542423 | 8/2015 |
| CN | 104921830 | 9/2015 |
| CN | 105146906 | 12/2015 |
| CN | 105581505 | 5/2016 |
| CN | 105640662 | 6/2016 |
| CN | 205307131 | 6/2016 |
| CN | 205359687 | 7/2016 |
| CN | 105943179 | 9/2016 |
| CN | 106109041 | 11/2016 |
| DE | 99427 | 9/1897 |
| DE | 1 632 384 | 6/1971 |
| DE | 2 209 562 | 9/1973 |
| DE | 2901136 | 7/1980 |
| DE | 8134787 | 5/1983 |
| DE | 86 10 513.2 | 8/1986 |
| DE | 3724476 | 1/1989 |
| DE | 40 29 770 | 3/1992 |
| DE | 94 17 795 | 5/1994 |
| DE | 690 21 971 | 5/1996 |
| DE | 297 03 210 | 4/1997 |
| DE | 195 41 429 | 5/1997 |
| DE | 295 20 454 | 6/1997 |
| DE | 29 807 736 | 11/1998 |
| DE | 29904059 | 7/1999 |
| DE | 200 18 077 | 2/2001 |
| DE | 10023725 | 11/2001 |
| DE | 202 09 014 | 10/2002 |
| DE | 202 16 413 | 2/2003 |
| DE | 20 2004 004 628 | 9/2004 |
| DE | 103 47 258 | 5/2005 |
| DE | 20 2005 015 767 | 2/2006 |
| DE | 20 2005 019 681 | 6/2006 |
| DE | 10 2006 005 205 | 9/2006 |
| DE | 10 2005 014 095 | 10/2006 |
| DE | 20 2009 013 323 | 4/2010 |
| DE | 20 2014 003 540 | 9/2014 |
| DE | 20 2014 009 678 | 3/2015 |
| EA | 000234 | 2/1999 |
| EP | 0 494 878 | 7/1992 |
| EP | 0 634 151 | 1/1995 |
| EP | 1 367 957 | 12/2003 |
| EP | 1 657 485 | 5/2006 |
| EP | 2 218 559 | 8/2010 |
| EP | 2 229 917 | 9/2010 |
| EP | 2 253 359 | 11/2010 |
| EP | 2 253 360 | 11/2010 |
| EP | 2468213 | 6/2012 |
| EP | 2528471 | 11/2017 |
| ES | 1 141 731 | 7/2015 |
| FR | 341238 | 8/1904 |
| FR | 2 790 383 | 9/2000 |
| GB | 2290702 | 1/1996 |
| GB | 2 406 503 | 4/2005 |
| GB | 2538300 | 11/2016 |
| GB | 2538302 | 11/2016 |
| GB | 2538304 | 11/2016 |
| GB | 2555417 | 5/2018 |
| JP | 62-102433 U | 6/1987 |
| JP | 5-18516 U | 3/1993 |
| JP | 2531600 | 6/1993 |
| JP | 5-237014 | 9/1993 |
| JP | 7-148020 | 6/1995 |
| JP | 10-113230 | 5/1998 |
| JP | 11-103937 | 4/1999 |
| JP | 2000-201740 A | 7/2000 |
| JP | 2003-304933 | 10/2003 |
| JP | 2004-222839 | 8/2004 |
| JP | 2006-61486 A | 3/2006 |
| JP | 2007-14730 | 1/2007 |
| JP | 2007-516029 | 6/2007 |
| JP | 2009-129543 | 6/2009 |
| JP | 2009-268828 | 11/2009 |
| JP | 2010-527717 | 8/2010 |
| JP | 2012-135567 | 7/2012 |
| JP | 2012-161368 | 8/2012 |
| JP | 2012-521787 | 9/2012 |
| JP | 2014-200297 | 10/2014 |
| JP | 2015-163091 | 9/2015 |
| JP | 2017-164214 | 9/2017 |
| KR | 10-2007-000010108 | 1/2007 |
| KR | 10-2010-0025434 | 3/2010 |
| KR | 10-2014-0049050 | 4/2014 |
| KR | 10-1594087 | 2/2016 |
| WO | WO-90/12557 | 11/1990 |
| WO | WO-92/02159 | 2/1992 |
| WO | WO-02/071971 | 9/2002 |
| WO | 2004/021958 | 3/2004 |
| WO | WO-2006/134514 | 12/2006 |
| WO | WO-2008/046580 | 4/2008 |
| WO | WO-2010/055435 | 5/2010 |
| WO | WO-2010/106524 | 9/2010 |
| WO | WO-2011/094587 | 8/2011 |
| WO | 2014/141211 | 9/2014 |
| WO | 2016/185166 | 11/2016 |
| WO | 2016/201063 | 12/2016 |
| WO | 2017/182301 | 10/2017 |

OTHER PUBLICATIONS

Follows et al., U.S. Office Action dated Apr. 6, 2017, directed to U.S. Appl. No. 15/152,116; 16 pages.

Follows et al., U.S. Office Action dated Mar. 12, 2019, directed to U.S. Appl. No. 15/804,284; 9 pages.

Mighall et al., U.S. Office Action dated Sep. 6, 2018, directed to U.S. Appl. No. 15/793,337; 13 pages.

International Search Report and Written Opinion dated Jan. 4, 2018, directed to International Application No. PCT/GB2017/053138; 9 pages.

Notice of Reasons for Rejection dated Jan. 24, 2019, directed to JP Application No. 2017-205881; 9 pages.

Mighall et al., U.S. Office Action dated May 13, 2019, directed to U.S. Appl. No. 15/793,337; 11 pages.

* cited by examiner

CLEANING APPLIANCE

REFERENCE TO RELATED APPLICATIONS

This application claims the priority of United Kingdom Application No. 1618075.4, filed Oct. 26, 2016, the entire contents of which are incorporated herein by reference.

FIELD OF THE INVENTION

The present invention relates to a cleaning appliance. The cleaning appliance is preferably a handheld cleaning appliance, and is preferably a surface treating appliance. In preferred embodiments of the invention, the appliance is a dental cleaning appliance. In a preferred embodiment, the appliance is an electric toothbrush having a fluid delivery system for delivering a fluid to the teeth of the user. This fluid may be toothpaste, or a fluid for improved interproximal cleaning. Alternatively, the appliance may not include any bristles or other elements for brushing teeth, and may be in the form of a dedicated interproximal cleaning appliance. The invention also relates to a handle for use with a dental cleaning appliance or a personal care appliance.

BACKGROUND OF THE INVENTION

Electric toothbrushes generally comprise a cleaning tool which is connected to a handle. The cleaning tool comprises a stem and a brush head bearing bristles for brushing teeth. The brush head comprises a static section which is connected to the stem, and at least one moveable section which is moveable relative to the static section, for example with one of a reciprocating, oscillating, vibrating, pivoting or rotating motion, to impart a brushing movement to bristles mounted thereon. The stem houses a drive shaft which couples with a transmission unit within the handle. The transmission unit is in turn connected to a motor, which is driven by a battery housed within the handle. The drive shaft and the transmission unit convert rotary or vibratory motion of the motor into the desired movement of the moveable section of the brush head relative to the static section of the brush head.

It is known to incorporate into an electric toothbrush an assembly for generating a jet of fluid for interproximal cleaning. For example, U.S. Pat. No. 8,522,384 describes an electric toothbrush in which the handle of the toothbrush defines a fluid chamber for storing a liquid such as water, and a slidable cover for enabling the fluid chamber to be accessed for replenishment by a user. A fluid path connects the fluid chamber to a nozzle located on a static portion of the brush head. A pump located within the fluid path is actuated upon user operation of an actuator on the handle to pump fluid from the fluid chamber to the nozzle for release under pressure from the nozzle.

SUMMARY OF THE INVENTION

In a first aspect, the present invention provides a dental cleaning appliance comprising a handle; a display; and a control circuit for activating the display; wherein the handle comprises a body and a transparent panel connected to the body, the panel defining a trough-shaped recess, and wherein the display is located beneath the recess.

The appliance preferably comprises a fluid reservoir, a fluid port through which the fluid reservoir is replenished and a fluid delivery system for receiving working fluid from the fluid reservoir. The working fluid is preferably a liquid, such as water or a water solution. To facilitate the replenishment of the fluid reservoir, the recess of the transparent panel of the handle may be shaped to guide working fluid from a tap towards the fluid port. As the working fluid passes over the recess, the external surface of the recess is cleaned.

The fluid port is preferably located in an external wall of the fluid reservoir. A bung or other closure member may be removably located within the fluid port to inhibit leakage of working fluid from the fluid reservoir through the fluid port. In a preferred embodiment, the fluid reservoir comprises a closure member which is pivotably connected thereto for movement between an open position, in which the fluid port is exposed by the closure member, and a closed position in which part of the closure member is located within the fluid port. The closure member is preferably located adjacent to the recess of the panel of the handle to facilitate the gripping of the closure member by the user.

The fluid reservoir preferably comprises an arm which is connected at one end thereof to the closure member and connected at the other end thereof to the fluid reservoir. The arm may be pivotably connected to the fluid reservoir. Alternatively, the arm may be flexible to allow the closure member to move relative to the fluid chamber. As another alternative, the arm may comprise a hinge located between the ends of the arm which allows said one end of the arm and the closure member to pivot relative to the other end of the arm and the fluid reservoir. As the closure member moves from the open position to the closed position, the arm of the closure member flexes outwardly away from the fluid reservoir. The recess of the handle is preferably positioned so that the arm enters the recess as the closure member moves from the open position to the closed position, thus allowing the arm to move unhindered relative to the fluid reservoir.

The closure member may be formed from resilient material to enable a fluid-tight seal to be formed between the closure member and the fluid port, and to allow the closure member to flex out from the fluid port as it moves from the closed position to the open position. Alternatively, the closure member may comprise a resilient sealing member, such as an o-ring, which forms a fluid-tight seal with the fluid port. The fluid port is preferably located in an external wall of the fluid reservoir, preferably a side portion of the external wall, and the arm is preferably connected to a bottom wall of the fluid reservoir which faces, and preferably engages, an end wall of the handle when the cleaning tool is connected to the handle. Part of the arm, which is preferably located between the hinge and said other end of the arm, is preferably received within a recessed section of the bottom wall of the fluid reservoir when the closure member is in its closed position so that the bottom surface of the arm is substantially flush with the bottom wall of the fluid reservoir.

The recess of the handle preferably has a cross-section orthogonal to the longitudinal axis of the handle which is curved, and is preferably concave in shape. The recess is preferably defined by a concave wall of the panel of the handle. The concave wall preferably extends substantially the length of the recess. The concave wall preferably has a cross-section which is arcuate in shape, having a radius of curvature which is preferably in the range from 5 to 10 mm. The concave wall preferably has a thickness in the range from 1 to 2 mm.

The body of the handle is preferably convex in shape. The body is preferably substantially cylindrical in shape, but the body may have an alternative cross-section orthogonal to the longitudinal axis of the handle, such as elliptical or polygonal. The cross-section may be symmetrical or asymmetrical.

The radius of curvature of the concave wall is preferably smaller than the radius of curvature of the body. The radius of curvature of the body is preferably in the range from 10 to 20 mm. The thickness of the body is preferably in the range from 0.7 to 1.5 mm.

The panel is preferably formed from a different material from at least an adjoining portion of the body of the handle. At least the portion of the body which adjoins the panel, and more preferably the entirety of the body, is preferably overmolded on to the panel. The body of the handle is preferably formed from an amorphous material, such as a blend of polycarbonate (PC) and acrylnitrile-butadiene-styrene (ABS) materials. The panel is preferably formed from a transparent polycarbonate material. The body preferably comprises an end surface which is located adjacent to the fluid reservoir. The recess preferably adjoins the end surface of the body. The handle preferably comprises an end wall located at the end of the body which is remote from the recess. The end wall may be detachable from the body to allow a user to replace a battery located within the handle.

The handle preferably comprises at least one user-operable button having a flexible membrane which is pressed by the user to operate the button. In a preferred embodiment, the handle comprises a plurality of such buttons which are defined by a common membrane. The membrane is preferably molded on to the panel, or vice versa, preferably before the body is overmolded on to the panel. The handle may comprise a plurality of flexible membranes overmolded on to the panel, or to which the panel is overmolded. The membranes may be disposed on opposite sides of the panel. The, or each, flexible membrane is preferably formed from a thermoplastic elastomeric material.

The body of the handle may be coated with a layer of paint. When the body is formed from an amorphous material, the paint layer can provide a barrier against chemical attack of the body. Prior to the painting of the body of the handle, the external surfaces of the panel and the flexible membrane(s) are masked to prevent those surfaces from being painted. Once the mask has been removed from the panel, a layer of reflective material may be disposed on an external surface of the panel and through which, during use, the activated display is visible to the user. This can improve the visual appearance of the handle; when the display is not activated it is not visible to the user through the layer of reflective material, whereas when the display is activated the display is visible to the user through the layer of reflective material.

In a second aspect, the present invention provides a dental cleaning appliance comprising a handle; a display; and a control circuit for activating the display; wherein the handle comprises a body which is gripped by a user during use of the appliance, a transparent panel beneath which the display is located, and a layer of reflective material disposed on an external surface of the panel and through which, during use, the activated display is visible to the user.

The layer of reflective material preferably has a transmissivity of at least 70%. The transmissivity of the reflective material is preferably in the range from 70 to 90%, more preferably in the range from 75 to 85%. The layer of reflective material is preferably applied to the panel using a printing process, preferably a hot stamping process in which a foil of reflective material is attached to the external surface of the panel. The reflective material is preferably formed from one of a polyester or a polycarbonate material which forms a thermo-chemical bond with the material of the transparent panel during the hot stamping process.

The foil or layer of reflective material is preferably applied to the panel after the body of the handle has been painted, and after any masking material has been removed following painting. Alternatively, the panel of transparent material may be overmolded on to a foil of the reflective material before the flexible membrane is formed on the panel.

As an alternative to painting the body of the handle, the body may be formed from a semi-crystalline material, for example a polyester such as PCTG or PET. In this case, the foil of reflective material may be applied to the panel after the body has been formed on the panel.

A transparent scratch-resistant coating may be applied over the body and the foil of reflective material. The scratch-resistant coating may be formed from a silicone material. Rigid end caps may also be attached, for example, using glue, to the exposed surfaces of the flexible membranes.

The display is an electronic display which is activated by the control circuit to display information to a user. The display preferably comprises an elongate display, and is preferably an OLED display.

The appliance preferably comprises a cleaning tool connected to the handle. The cleaning tool preferably comprises a head, and a stem extending between the head and the handle. The cleaning tool preferably comprises the fluid reservoir. The fluid reservoir is preferably connected to, and preferably extends around, the stem. The head preferably comprises a nozzle of the fluid delivery system for delivering a burst of working fluid to the teeth of a user. The working fluid is preferably a liquid working fluid, which is preferably water or a water solution.

The fluid delivery system preferably comprises a pump and a control circuit for actuating the pump to draw working fluid from the fluid reservoir and eject a burst of working fluid towards the nozzle. As the nozzle is moved between adjacent teeth of the user, the user may depress one of the user-operable buttons to actuate the pump to cause a burst of working fluid to be ejected from the nozzle. Alternatively, the appliance may be configured to actuate the delivery of working fluid to the teeth of the user automatically depending on the magnitude of an output from a sensor for detecting that the nozzle is located within an interproximal gap. For example, the sensor may be in the form of a light detector, such a camera or a light sensor, for receiving light, such a visible light or infrared light, reflected from a user's teeth. As another alternative, the appliance may be configured to actuate the delivery of working fluid to the teeth of the user automatically at a fixed frequency, for example between 0.5 and 5 Hz.

The appliance may be in the form of a dedicated interproximal cleaning appliance for cleaning between the gaps in the user's teeth. Alternatively, the appliance may be in the form of a toothbrush which has the additional function of improved interproximal cleaning through the emission of a burst of working fluid into the interproximal gap. Where the appliance is in the form of a toothbrush, the cleaning tool preferably comprises a plurality of bristles. The bristles are preferably arranged around the nozzle, and may be arranged circumferentially about the nozzle. A plurality of bristles may be attached to a static section of the cleaning tool, which section is not moveable relative to the handle. Alternatively, or additionally, a plurality of bristles may be attached to a moveable section of the cleaning tool, which section is moveable relative to the handle. In a preferred embodiment, the appliance comprises a brush unit comprising a bristle carrier and a plurality of bristles mounted on the bristle carrier, with the bristle carrier being moveable relative to the handle.

The cleaning tool is preferably detachably connected to the handle. This can allow the appliance to be provided with a set of similar cleaning tools, each with a respective different identifier. This can also allow an appliance to be provided with a set of dissimilar stems or cleaning tools. For example, the set of cleaning tools may be selected from two or more of a first type of cleaning tool with a nozzle and a moveable brush unit, a second type of cleaning tool with a nozzle and a static brush unit, and a third type of cleaning tool with a nozzle and no bristles. A number of respective different cleaning tools of the same type may also be provided, for example, of the first type of cleaning tool, with bristles having a respective different stiffness, or with nozzles having respective different fluid outlet sizes.

The handle of the appliance may also be provided separately from the cleaning tool, for example as a spare part for the appliance, or for use by a different user. For example, handles having respective different shapes may be provided for use by users of different age.

The invention has been described above in connection with a cleaning appliance, but the invention may also be used with other personal care appliances, such as mirrors, electric razors, hair dryers, hair straighteners, and hot styling brushes.

In a third aspect, the present invention provides a handle for a personal care appliance, preferably a dental cleaning appliance, the handle being detachably connectable to a tool of the appliance, the handle comprising a body; a transparent panel connected to the body, the panel defining a trough-shaped recess; a display; and a control circuit for activating the display; wherein the display is located beneath the recess.

In a fourth aspect, the present invention provides a handle for a personal care appliance, preferably a dental cleaning appliance comprising a cleaning tool to which the handle is detachably connectable, the handle comprising a display; a control circuit for activating the display; and a body which is gripped by a user during use of the appliance; a transparent panel beneath which the display is located; and a layer of reflective material disposed on an external surface of the panel and through which, during use, the activated display is visible to the user.

One or more of the aforementioned aspects of the invention may also be applied more generally to cleaning apparatus or a cleaning appliance. The apparatus may be a surface treating appliance. For example, the apparatus may be in the form of apparatus, preferably a handheld apparatus, for cleaning a work surface, in which the brush unit is arranged to engage a work surface and the nozzle is arranged to deliver cleaning fluid to the work surface during cleaning.

In a fifth aspect, the present invention provides a method of manufacturing a handle for a dental cleaning appliance, the method comprising the steps of forming a transparent panel; overmolding on to the panel a body to be gripped by the user; forming, preferably using a hot stamping process, a layer of reflective material on an external surface of the panel; and locating an electronic display beneath the panel; wherein the reflective material has a transmissivity of at least 70% to enable the display, when activated, to be visible to the user during use of the appliance.

In a sixth aspect, the present invention provides a method of manufacturing a handle for a dental cleaning appliance, the method comprising the steps of forming a foil of reflective material; overmolding on to the foil a transparent panel; overmolding on to the panel a body to be gripped by the user; and locating an electronic display beneath the panel; wherein the reflective material has a transmissivity of at least 70% to enable the display, when activated, to be visible to the user during use of the appliance.

Features described above in connection with the first aspect of the invention are equally applicable to each of the second to sixth aspects of the invention, and vice versa.

BRIEF DESCRIPTION OF THE DRAWINGS

Preferred features of the present invention will now be described by way of example only with reference to the accompanying drawings, in which.

DETAILED DESCRIPTION OF THE INVENTION

Figure 1A:
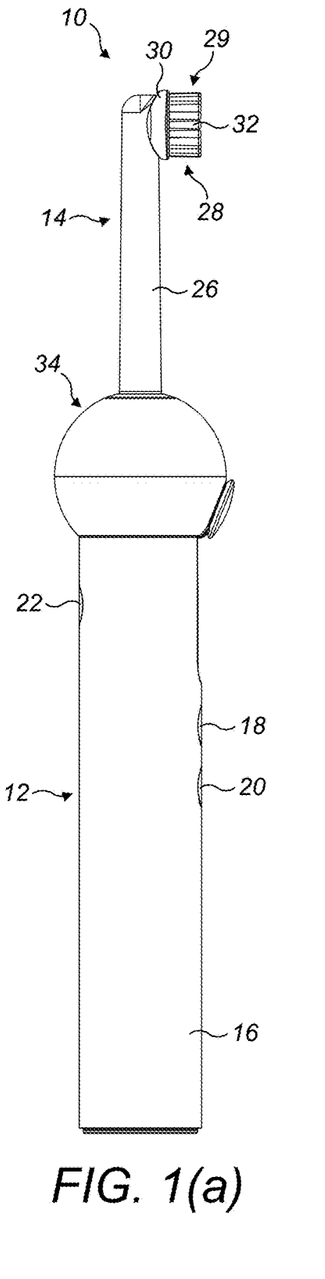
FIG. 1(a) is a right side view of a dental cleaning appliance.
Figure 1B:
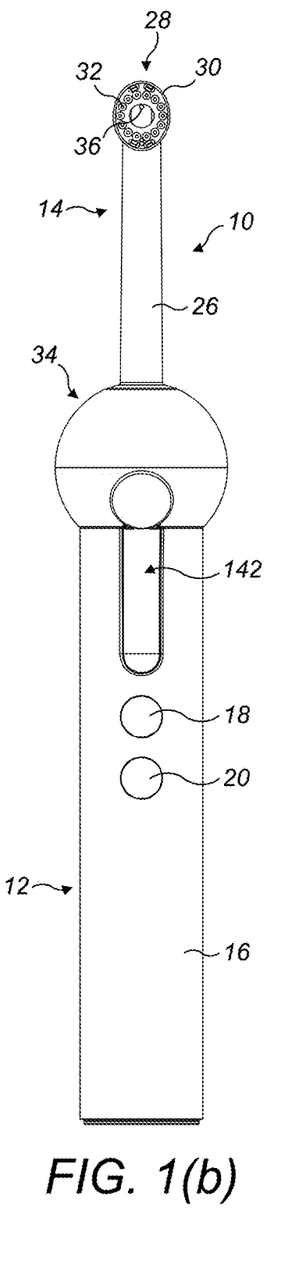
FIG. 1(b) is a front view of the appliance.
Figure 1C:
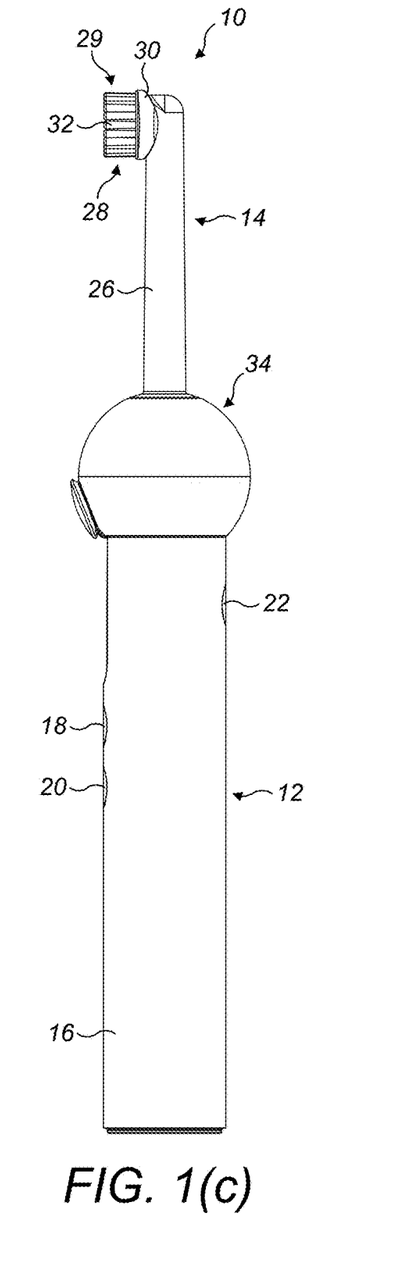
FIG. 1(c) is a left side view of the appliance.

FIGS. 1(a) to 1(c) illustrate external views of an embodiment of a dental cleaning appliance 10. In this embodiment, the appliance is in the form of a handheld appliance, which is in the form of an electric toothbrush having an integrated assembly for dispensing a working fluid for improved interproximal cleaning.

The appliance 10 comprises a handle 12 and a cleaning tool 14. The handle 12 comprises a body 16 which is gripped by a user during use of the appliance 10. The body 16 is preferably formed from plastics material, and is preferably generally cylindrical in shape. The handle 12 comprises a plurality of user operable buttons 18, 20, 22 which are located within respective apertures formed in the body 16 so as to be accessible to the user. As discussed in more detail below, the handle 12 also comprises an electronic display 24. The display is preferably an elongate display, insofar as the display 24 has a length which is greater than its width, and is preferably in the form of an OLED display.

The cleaning tool 14 comprises a stem 26 and a head 28. The stem 26 is elongate in shape, which serves to space the head 28 from the handle 12 to facilitate user operability of the appliance 10. In this embodiment, the head 28 of the cleaning tool 14 comprises a brush unit 29, which comprises a bristle carrier 30 and a plurality of bristles 32 mounted on the bristle carrier 30. However, in other embodiments the cleaning tool 14 may be provided without a brush unit 29 so that the appliance is in the form of a dedicated interproximal cleaning appliance for cleaning between the gaps in the user's teeth.

The cleaning tool 14 also comprises a fluid reservoir 34 for storing a working fluid, and a nozzle 36 for delivering one or more bursts of working fluid to the teeth of the user during use of the appliance 10. The fluid reservoir 34 is connected to the stem 26. The fluid reservoir 34 extends at least partially around the stem 26. In this embodiment which includes a brush unit 29, the brush unit 29 extends at least partially around the nozzle 36.

The nozzle 36 forms part of a fluid delivery system 40 for receiving working fluid from the fluid reservoir 34 and for delivering bursts of working fluid to the teeth of a user during use of the appliance 10. Each burst of working fluid preferably has a volume which is less than 1 ml, more preferably less than 0.5 ml, and in this example is around 0.25 ml. The tip of the nozzle 36 comprises a fluid outlet 42 through which a burst of working fluid is delivered to the teeth of the user. The fluid delivery system 40 is illustrated schematically in FIG. 2. In overview, the fluid delivery system 40 comprises a fluid inlet 44 for receiving working fluid from the fluid reservoir 34. In this embodiment, the working fluid is a liquid working fluid, which is preferably water. The fluid delivery system 40 comprises a pump assembly for drawing working fluid from the fluid reservoir 34 through the fluid inlet 44, and for delivering a burst of working fluid to the nozzle 36. The pump assembly is located within the handle 12, and comprises a positive displacement pump 48 and a drive for driving the pump 48. The drive preferably comprises a motor 50. A battery 52 for supplying power to the motor 50 is also located in the handle 12. The battery 52 is preferably a rechargeable battery.

Figure 2:
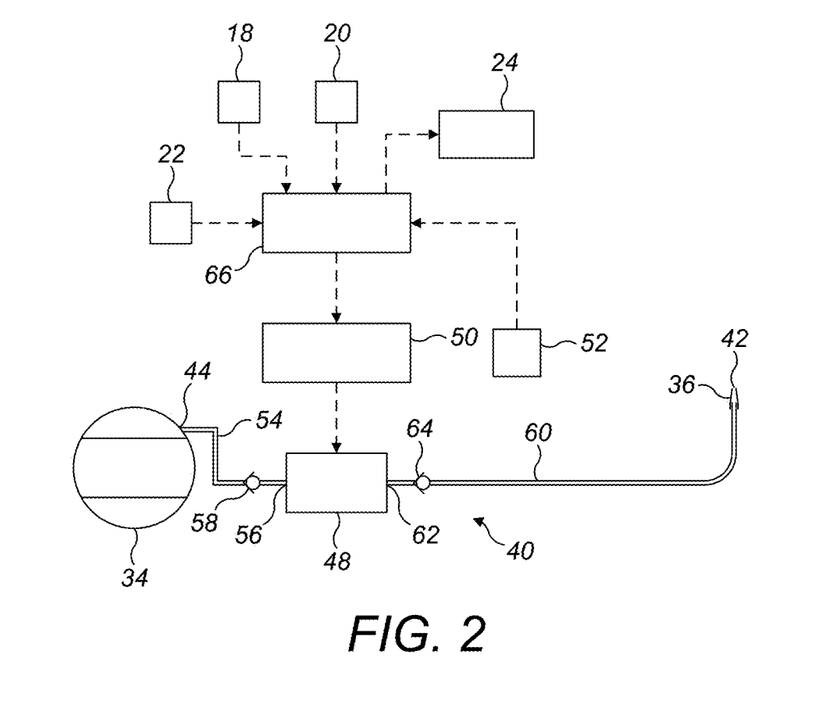
FIG. 2 illustrates schematically components of a fluid delivery system for delivering a burst of a working fluid to the teeth of a user.

A first conduit 54 connects the fluid inlet 44 of the fluid delivery system 40 to a fluid inlet 56 of the pump 48. A first one-way valve 58 is located between the fluid inlet 44 and the pump 48 to prevent water from returning to the fluid reservoir 34 from the pump 48. A second conduit 60 connects a fluid outlet 62 of the pump 48 to the nozzle 36. A second one-way valve 64 is located between the pump 48 and the nozzle 36 to prevent water from returning to the pump 48. A control circuit 66 controls the actuation of the motor 50, and so the motor 50 and the control circuit 66 provide a drive for driving the pump 48. The battery 52 supplies power to the control circuit 66. The control circuit 66 includes a motor controller, which supplies power to the motor 50.

In this embodiment, the control circuit 66 receives signals generated when the user depresses the buttons 18, 20, 22 located on the handle 12 of the appliance 10. Alternatively, or additionally, the control circuit 66 may receive signals which are generated by a sensor located within the appliance, or which are received from a remote device, such as a display or a personal device. For brevity, in the following description the control circuit 66 receives signals which are generated when the user operates one of the buttons 18, 20, 22. The control circuit 66 also controls the activation of the display 24.

Figure 3:
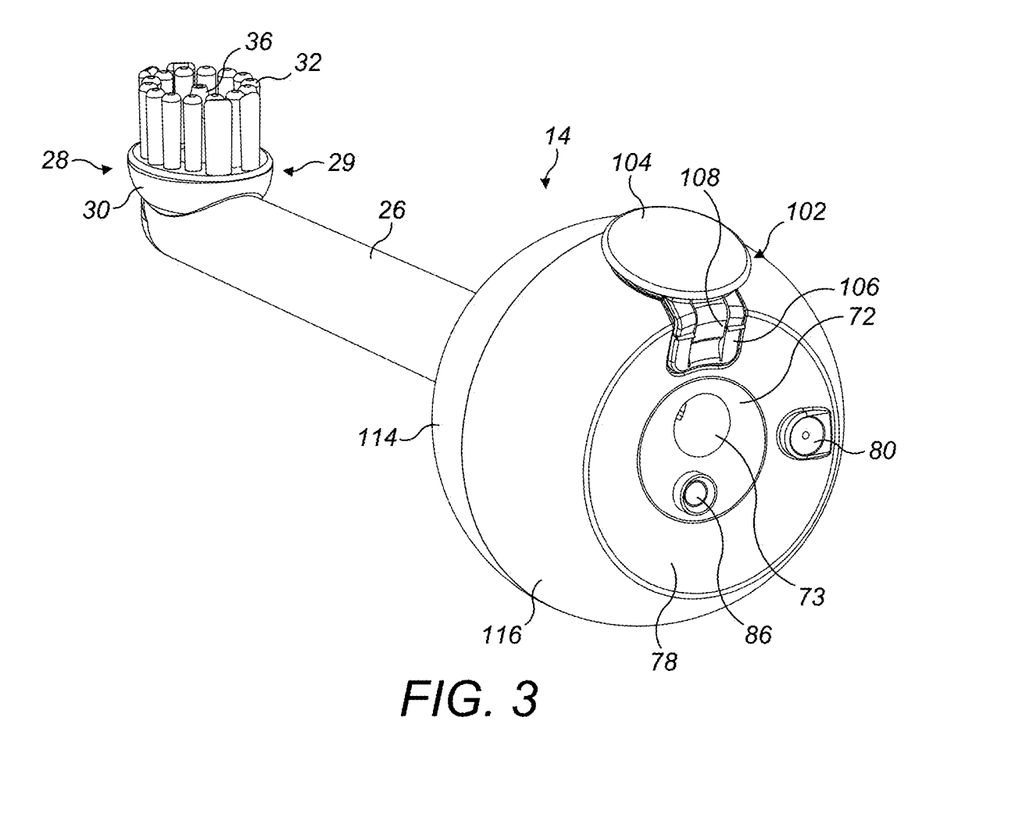
FIG. 3 is a right side perspective view, from above, of a cleaning tool of the appliance.
Figure 4:
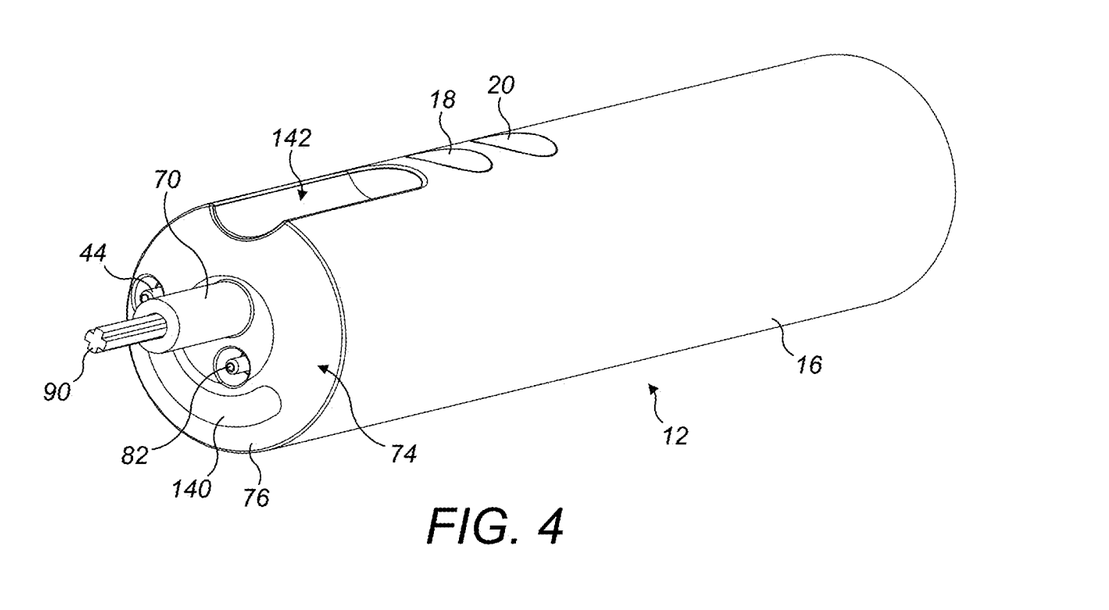
FIG. 4 is a right side perspective view, from above, of a handle of the appliance.
Figure 5:
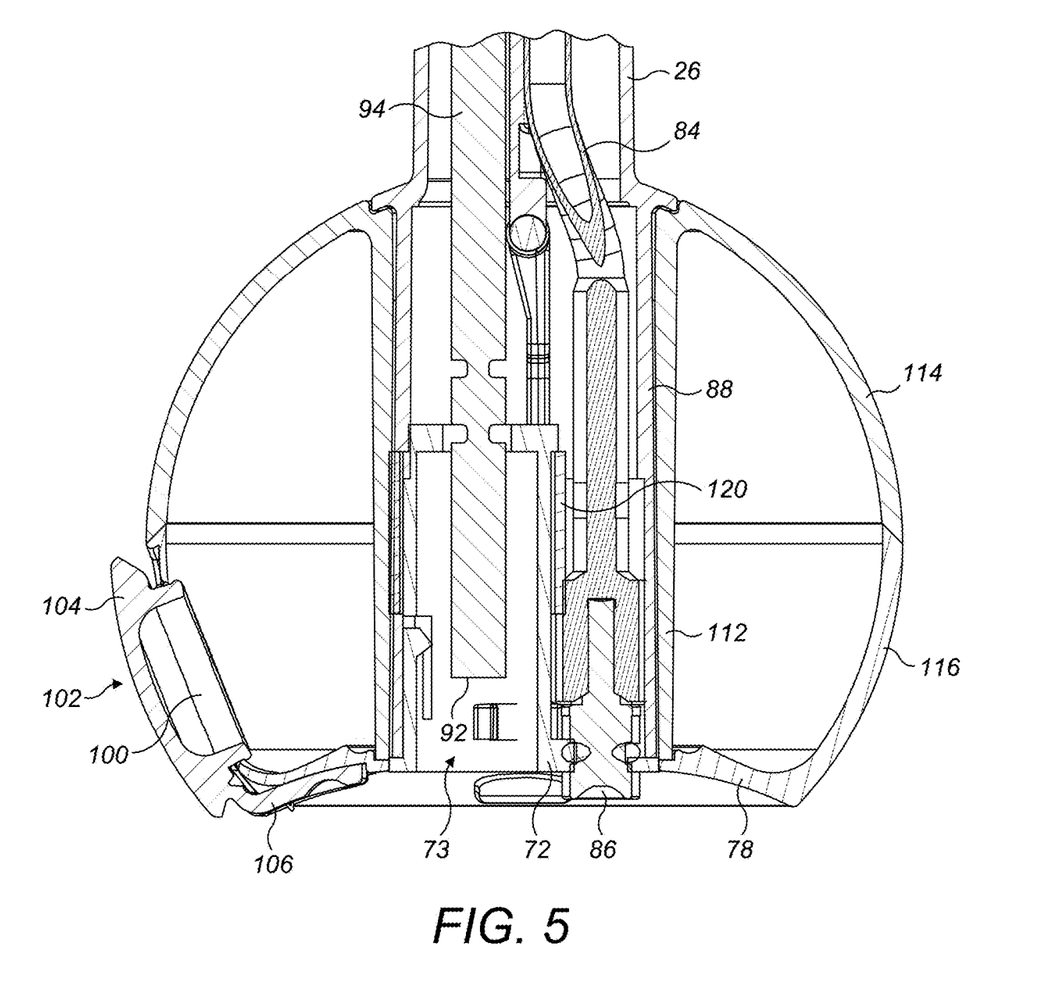
FIG. 5 is a side sectional view of a lower part of the cleaning tool.

The cleaning tool 14 is detachably connected to the handle 12. With reference to FIGS. 3 to 5, the handle 12 comprises a male connector, preferably in the form of a spigot 70, which is received by a complementary female connector, preferably in the form of a recessed connector 72, of the cleaning tool 14. The recessed connector 72 defines a generally cylindrical recess 73 for receiving the spigot 70. The spigot 70 preferably protrudes outwardly from an end wall 74 of the body 16, and preferably in a direction which is parallel to a longitudinal axis of the handle 12. The end wall 74 defines an annular seat 76 for receiving an annular bottom wall 78 of the fluid reservoir 34 when the cleaning tool 14 is mounted on the handle 12. The annular seat 76 comprises the fluid inlet 44 of the fluid delivery system 40. The fluid inlet 44 receives fluid from a reservoir fluid outlet port 80 of the fluid reservoir 34 when the cleaning tool 14 is mounted on the handle 12.

The second conduit 60, which connects the fluid outlet 62 of the pump 48 to the nozzle 36, comprises a handle conduit section located within the handle 12, and a cleaning tool conduit section located within the cleaning tool 14. The handle conduit section extends from the fluid outlet 62 of the pump 48 to a handle fluid outlet port 82 located adjacent to the spigot 70. The cleaning tool conduit section 84 comprises a cleaning tool fluid inlet port 86 for receiving fluid from the handle fluid outlet port 82 when the cleaning tool 14 is connected to the handle 12. The cleaning tool fluid inlet port 86 protrudes from the base of the recessed connector 72. The recessed connector 72 is housed within, and connected to, a relatively wide base section 88 of the stem 26.

As mentioned above, the cleaning tool 14 includes a bristle carrier 30 which is moveable relative to the stem 26. The appliance 10 comprises a drive mechanism for driving the movement of the bristle carrier 30 relative to the stem 26. The drive mechanism comprises a transmission unit connected to the bristle carrier 30, and a drive unit for driving the transmission unit to move the bristle carrier 30 relative to the stem 26.

The handle 12 comprises the drive unit of the drive mechanism. The drive unit comprises a motor, preferably in the form of a dc motor, which is actuated by the control circuit 66 in response to the user depression of one or more of the buttons of the handle 12. The motor of the drive unit is connected via a gear train to a rotatable drive unit coupling member 90 which protrudes outwardly from the spigot 70, and which rotates relative to the body 16 upon actuation of the motor of the drive unit.

The cleaning tool 14 comprises the transmission unit of the drive mechanism. The transmission unit comprises a transmission unit coupling member 92 which couples with, and preferably receives, the drive unit coupling member 90 when the cleaning tool 14 is connected to the handle 12. The transmission unit coupling member 92 is connected to, and is preferably integral with, one end of a connecting rod 94 housed within the stem 26. The other end of the connecting rod 94 is connected to the side surface of the bristle carrier 30 so that periodic rotation of the connecting rod 94 about a 15° angle results in a 15° sweeping movement of the bristle carrier 30 relative to the stem 26.

The fluid reservoir 34 is mounted on, and extends at least partially around, the stem 26 of the cleaning tool 14. In this embodiment, the fluid reservoir 34 is annular in shape, and so surrounds the stem 26. The fluid reservoir 34 is preferably located at or towards the end of the stem 26 which is remote from the head 28, and so in this embodiment extends around the base section 88 of the stem 26. The fluid reservoir 34 preferably has a capacity in the range from 5 to 50 ml, and in this embodiment has a capacity of 25 ml.

The fluid reservoir 34 is filled through a reservoir fluid inlet port 100 formed in the external wall of the fluid reservoir 34. The fluid inlet port 100 is preferably formed in an annular external side wall of the fluid reservoir 34. The reservoir fluid inlet port 100 is sealed by a closure member 102. The closure member 102 is moveable relative to the fluid reservoir 34 between a closed position, as shown in FIG. 3, in which the closure member 102 inhibits the leakage of working fluid from the reservoir fluid inlet port 100, and an open position. In this embodiment, the closure member 102 is pivotably connected to the fluid reservoir 34. The closure member 102 is locatable within, and forms a fluid-tight seal against, the reservoir fluid inlet port 100. The closure member 102 comprises a head 104 which may be gripped by the user to move the closure member 102 from the closed position to the open position, and which may be pushed by the user towards the reservoir fluid inlet port 100 to return the closure member 102 to the closed position.

The closure member 102 is connected to the fluid reservoir 34 by a pair of arms 106. One end of each arm 106 is connected to the closure member 102, and the other end of each arm 106 is connected to the fluid reservoir 34. In this embodiment, the arms 106 are integral with the closure member 102, with a portion of each arm 106 which is remote from the closure member 102 being connected to the bottom wall 78 of the fluid reservoir 34, for example using an adhesive or by welding. Each arm 106 comprises a hinge 108, which may be formed from a part of the arm 106 which has a locally reduced thickness, to enable the part of the arm 106 which is connected to the closure member 102 to pivot relative to the other part of the arm 106 which is connected to the fluid reservoir 34.

To fill the fluid reservoir 34, the user detaches the cleaning tool 14 from the handle 12, grips the head 104 of the closure member 102 between finger and thumb and pulls it out from the reservoir fluid inlet port 100. The fluid reservoir 34 may then be filled by the user, for example by locating the reservoir fluid inlet port 100 beneath a running tap. Once the fluid reservoir 34 has been filled, the user pushes the head 104 of the closure member 102 back into the reservoir fluid inlet port 100, and reconnects the cleaning tool 14 to the handle 12. The pivoting connection between the closure member 102 and the bottom wall 78 of the fluid reservoir 34 inhibits accidental loss of the closure member 102 while the reservoir fluid inlet port 100 is exposed, and enables the joint between the closure member 102 and the fluid reservoir 34 to be located between the handle 12 and the fluid reservoir 34 when the cleaning tool 14 is mounted on the handle 12. As shown in FIG. 3, the lower parts of the arms 106 of the closure member 102 are located within a recessed section of the bottom wall 78 of the fluid reservoir 34 when the closure member 102 is in its closed position so that the bottom surfaces of the lower parts of the arms 106 are substantially flush with the bottom wall 78 of the fluid reservoir 34.

At least part of the external wall of the fluid reservoir 34 is preferably transparent to allow a user to observe the contents of the fluid reservoir 34, and so assess whether the fluid reservoir 34 requires replenishment prior to the desired use of the appliance 10. The external wall preferably has a shape which is symmetrical about the longitudinal axis of the cleaning tool 14. The external wall preferably has a curved shape, more preferably a convex curved shape, but alternatively the external wall may have a polygonal or faceted shape. In this embodiment, the external wall has a spherical curvature. As described below, the fluid reservoir 34 is mounted on the relatively wide base section 88 of the stem 26, and so the external wall has opposed circular apertures which are centred on the longitudinal axis of the cleaning tool 14 to allow the base section 88 of the stem 26 to pass therethrough.

The fluid reservoir 34 further comprises an inner wall 112 which is connected to the external wall, and which with the external wall defines the capacity of the fluid reservoir 34. The inner wall 112 is tubular in shape. The ends of the inner wall 112 are preferably circular in shape, and are connected to the external wall so as to form a fluid-tight seal between the external wall and the inner wall 112. In this embodiment, the fluid reservoir 34 is formed from two housing parts. A first housing part 114 comprises an upper section of the external wall and the inner wall 112, and so the upper end of the inner wall 112 is integral with an upper section of the external wall. A second housing part 116 comprises a lower section of the external wall and the bottom wall 78 of the fluid reservoir 34.

To mount the fluid reservoir 34 on the stem 26, the circular aperture formed in the first housing part 114 of the fluid reservoir 34 is aligned with the free end of the base section 88 of the stem 26, and the fluid reservoir 34 is pushed on to the stem 26. The internal surface of the inner wall 112 of the fluid reservoir 34 bears against the base section 88 of the stem 26 so that frictional forces therebetween prevent the fluid reservoir 34 from falling from the stem 26. To mount the cleaning tool 14 on the handle 12, the spigot 70 of the handle 12 is aligned with the recess 73 formed in the connector 72 of the cleaning tool 14, and the handle fluid outlet port 82 located adjacent to the spigot 70 is aligned with the cleaning tool fluid inlet port 86 of the cleaning tool 14. The cleaning tool 14 is then pushed on to the spigot 70 so that the handle fluid outlet port 82 connects to the cleaning tool fluid inlet port 86, and so that the fluid reservoir 34 engages the annular seat 76 to connect the reservoir fluid outlet port 80 to the fluid inlet 44 of the fluid delivery system 40. The internal surface of the connector 72 of the stem 26 bears against the external surface of the spigot 70 so that frictional forces therebetween retain the stem 26 on the handle 12. The connector 72 is preferably formed from resilient plastics material which flexes as the connector 72 is pushed on to the spigot 70 to increase the frictional forces therebetween. A spring clip 120 may be provided at least partially about the connector 72 for urging the internal surface of the connector 72 against the spigot 70.

Turning now to FIGS. 6 to 10, as mentioned above the handle 12 of the appliance 10 comprises an external body 16 which is gripped by the user during use of the appliance 10. The body 16 forms part of an outer casing of the handle 12, which additionally comprises a transparent panel 130 and a foil 132 of reflective material. The panel 130 is formed from a transparent polycarbonate material. With particular reference to FIG. 6(a), the panel 130 has an annular end wall 134 and a side wall 136 depending from the end wall 134. The end wall 134 comprises an aperture 138 for receiving the fluid inlet 44 of the fluid delivery system 40, and a raised annular section 140 which provides a light emitter for emitting towards the fluid reservoir 34 light generated by a light source (not shown) located within the handle 12. The light source is activated by the control circuit 66 to generate a visual alert for the user. The side wall 136 of the panel 130 has the shape of a section of a cylinder. The side wall 136 defines a trough-shaped recess 142 on the external surface of the panel 130, which extends from the end wall 134 generally midway along the side wall 136. The recess 142 is defined by a concave section 144 of the side wall 136 of the panel 130. The concave section 144 has a generally arcuate shape, and has a radius of curvature which is smaller than the radius of the body 16 of the handle 12. In this embodiment, the radius of the body 16 is approximately 15 mm, whereas the radius of curvature of the concave section 144 of the side wall 136 of the panel is around 6 mm.

Figure 7A:
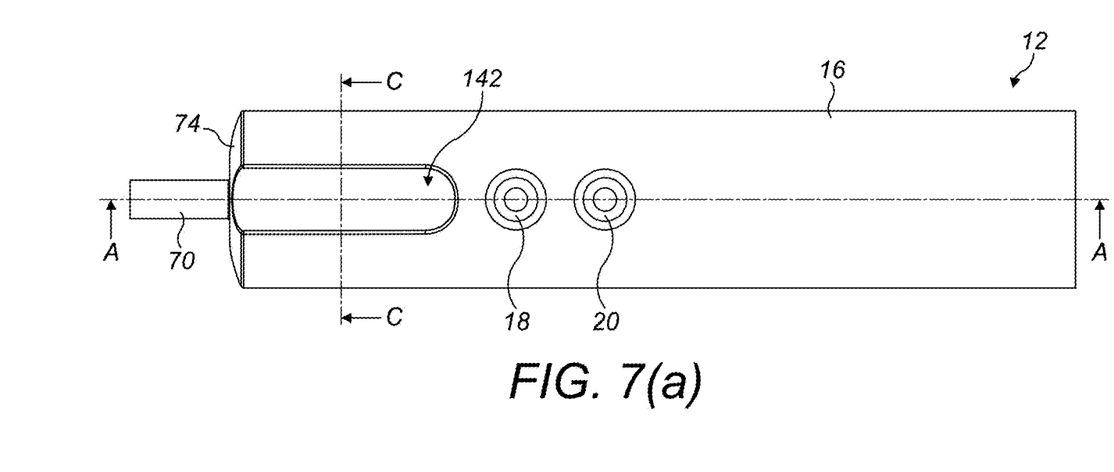
FIG. 7(a) is a front view of an assembled casing of the handle.
Figure 7B:
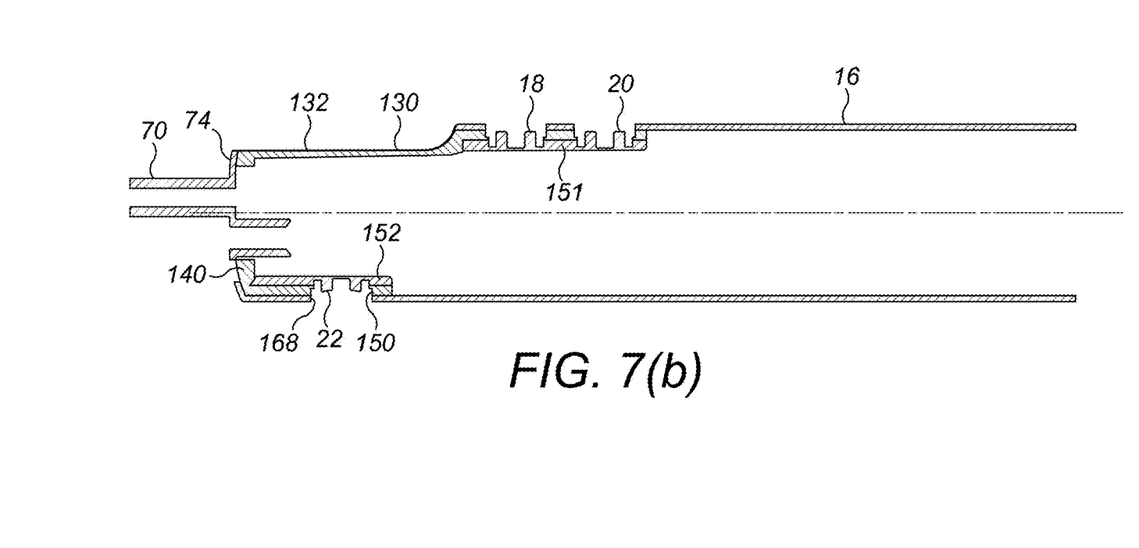
FIG. 7(b) is a side section through line A-A of FIG. 7(a)
Figure 7C:
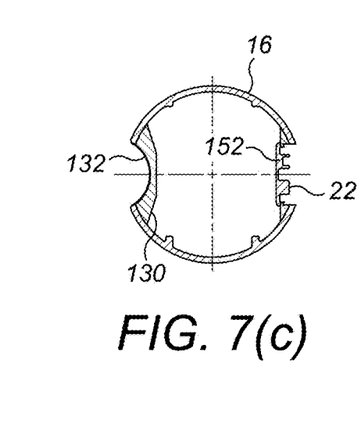
FIG. 7(c) is a bottom section through line C-C of FIG. 7(a)

The side wall 136 of the panel 130 also comprises circular apertures 146, 148, 150 for receiving the user-operable buttons 18, 20, 22 of the handle 12. As shown in FIGS. 7(a) to 7(c), the buttons 18, 20 are located on a first flexible membrane 151 which is connected to the internal surface of the panel 130 so that the buttons 18, 20 are manually accessible by the user through the apertures 146, 148. Button 22 is located on a second flexible membrane 152 also connected to the internal surface of the panel 130 so that the button 22 is manually accessible by the user through the aperture 150. The flexible membranes 151, 152 are preferably formed from a thermoplastic elastomeric material. The flexible membranes 151, 152 may be overmolded on to the panel 130. Alternatively, the panel 130 may be overmolded on to the flexible membranes 151, 152.

Figure 6A:
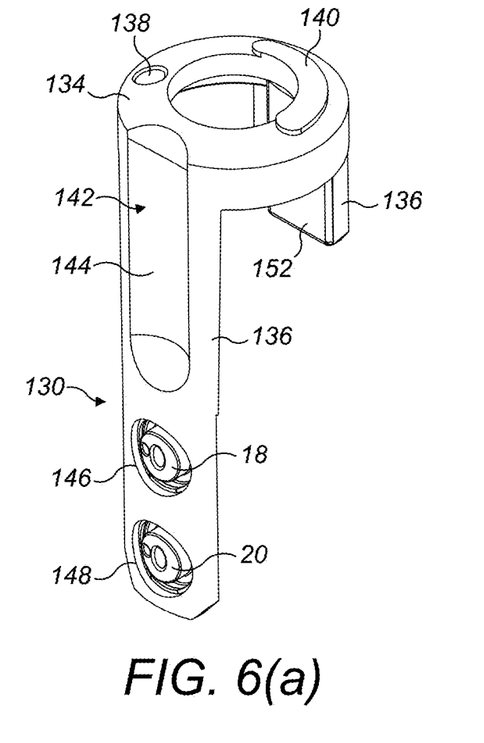
FIG. 6(a) is a perspective view of a transparent panel of the handle of the appliance.
Figure 6B:
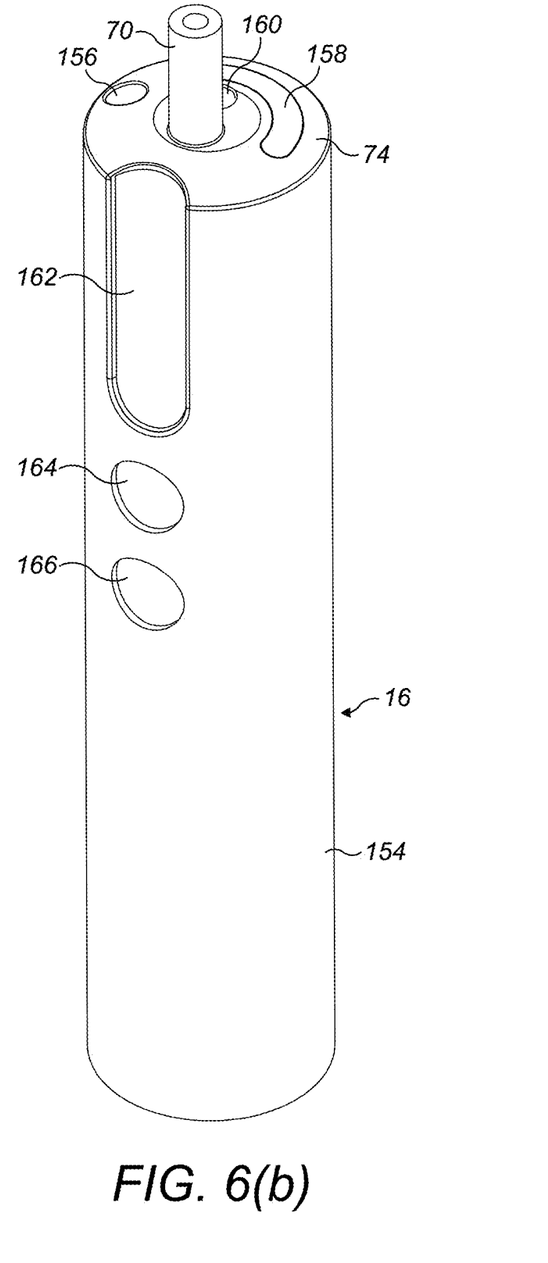
FIG. 6(b) is a perspective view of a body of the handle.

The body 16 is illustrated in FIG. 6(b). The body 16 is preferably formed from a blend of polycarbonate (PC) and acrylnitrile-butadiene-styrene (ABS) materials. The body 16 has an annular end wall 74 from which the spigot 70 protrudes, and a tubular side wall 154 of circular cross-section, the curvature of which is substantially equal to that of the side wall 136 of the panel 130. The end wall 74 comprises apertures 156, 158 which, when the casing is assembled, align with the aperture 138 and light emitter 140 of the panel 130 respectively. The end wall 74 also comprises an aperture 160 for receiving the handle fluid outlet port 82. The side wall 154 also comprises an aperture 162 having a perimeter with the same shape as the perimeter of the recess 142 of the panel 130 which aligns with the recess 142 when the casing is assembled. Circular apertures 164, 166, 168 in the side wall 154 also align with, and have the same shape as, the apertures 146, 148, 150 respectively when the casing is assembled. To assemble the casing, the body 16 is overmolded on to a sub-assembly comprising the panel 130 and the flexible membranes 151, 152. Following the overmolding of the body 16 on to the sub-assembly, the body 16 may be painted a desired color. The exposed light emitter 140, recess 142 and buttons 146, 148, 150 are masked before the body 16 is painted, preferably with a first layer of a base coat and a second layer of a pigment coat.

Figure 6C:
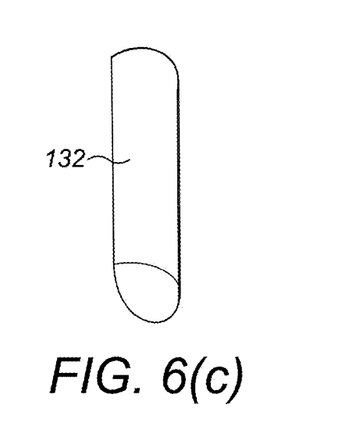
FIG. 6(c) is a perspective view of a foil of reflective material of the handle.

Following painting, the masks are removed and the foil 132 of reflective material is attached to the exposed external surface of the recess 142. The foil 132 of reflective material is illustrated in FIG. 6(c). The foil 132 is formed from one of a polyester and a polycarbonate material, which has a light transmissivity of at least 70%, preferably between 70 and 90% and more preferably between 75 and 85%. The foil 132 has substantially the same shape as the recess 142. In this embodiment, the foil 132 is attached to the external surface of the recess 142 using a printing process, preferably a hot stamping process which fuses the foil 132 to the panel 130. A scratch-resistant coating 170, indicated in FIG. 9, may then be applied over the external surface of the casing. Relatively rigid end caps, visible in FIGS. 1, 4 and 8 to 10, may be attached to the exposed external surfaces of the flexible membranes 151, 152, for example using an adhesive, for engagement by the user to actuate the buttons 18, 20, 22.

Alternatively, the foil 132 may be connected to the panel 130 before the body 16 is overmolded on to the panel 130, and preferably before the membranes 151, 152 are attached to the panel 130. For example, the body of the panel 130 may be molded on to the foil 132, for example using an injection molding process, before the membranes 151, 152 are attached to the panel 130.

Figure 8:
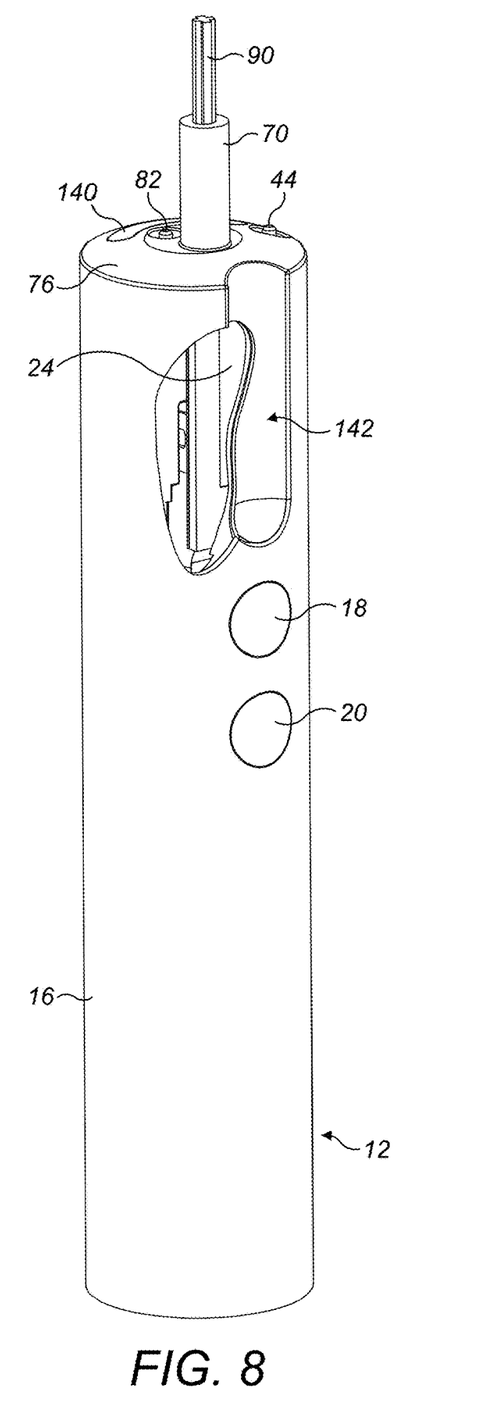
FIG. 8 is a perspective view of the handle, with part of the body of the handle removed to reveal an electronic display beneath a panel of the handle.
Figure 9:
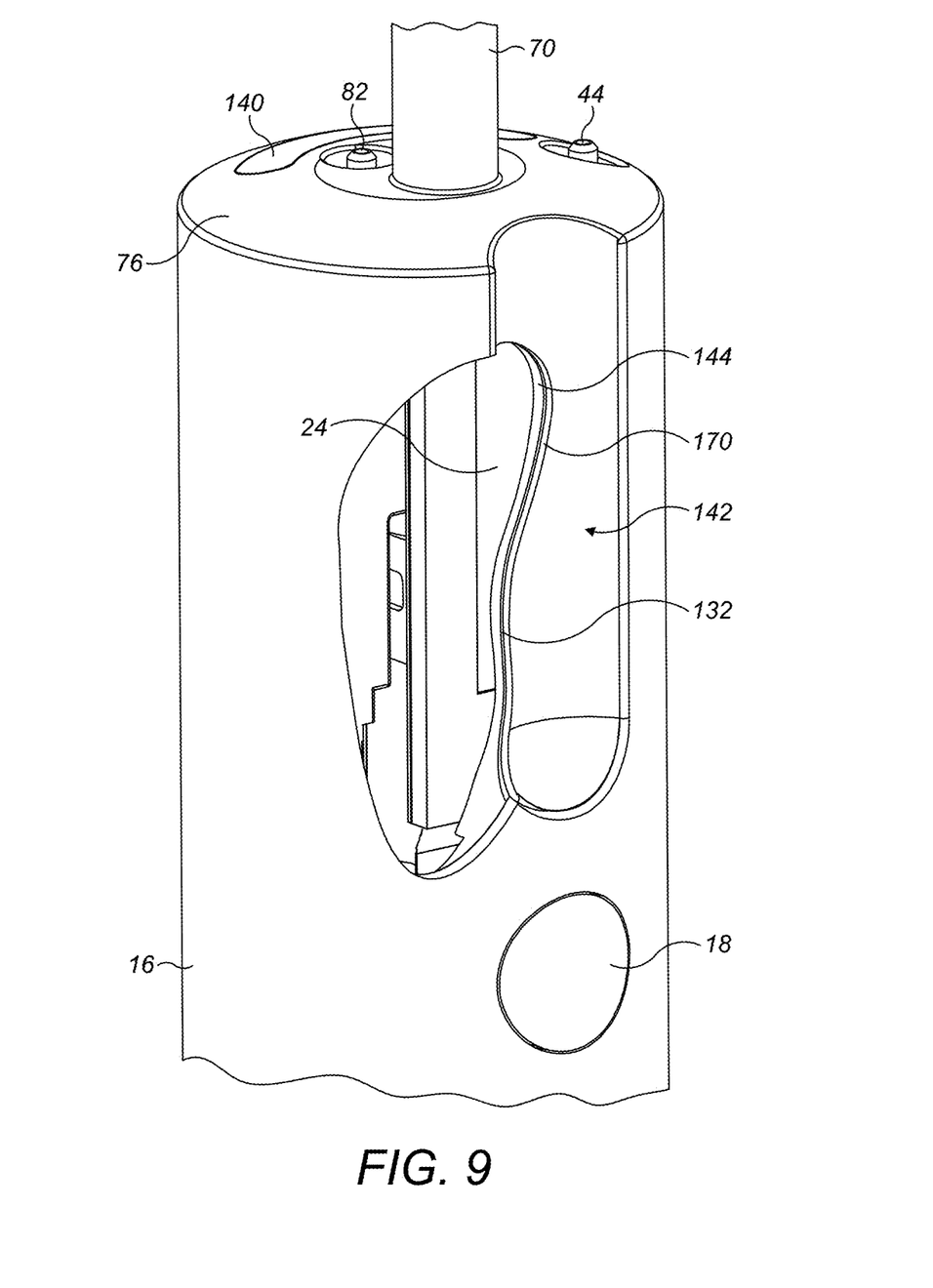
FIG. 9 is a close up of part of FIG. 8.
Figure 10:
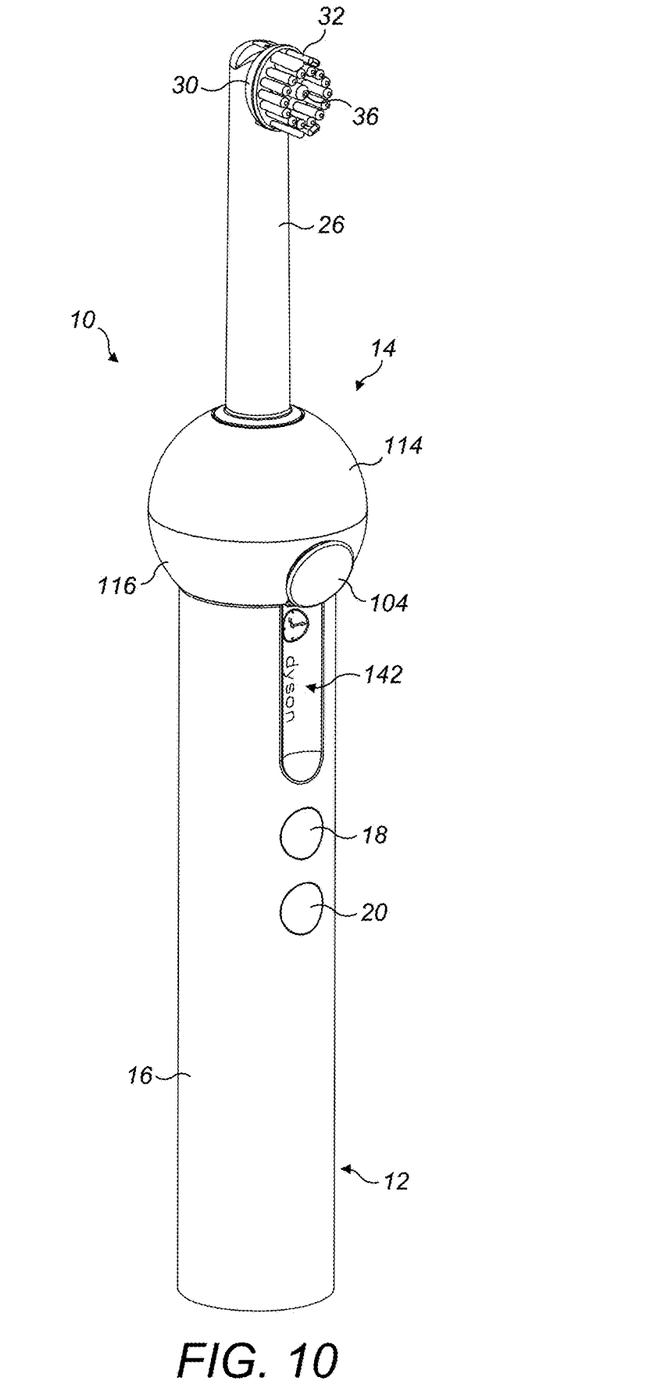
FIG. 10 is a perspective view of the appliance, with the activated display through the panel of the handle.

Once the casing of the handle 12 has been assembled, the internal components of the handle 12 are inserted into the handle 12 through the open end of the body 16. As mentioned above, the appliance 10 comprises an electronic display 24 which is actuable by the control circuit 66 to display alphanumerical and/or graphical characters to the user during a cleaning process. For example, the display 24 may indicate one or more of a selected cleaning mode, a time of operation, and a battery charging level. With reference to FIGS. 8 and 9, the display 24 is positioned within the handle 12 so that it is located directly beneath the recess 142 of the panel 130. The provision of a foil 132 of reflective material on the external surface of the recess 142 of the panel 130 prevents the display 24 from being visible to a user when the display 24 is not activated by the control circuit 66. The preferred transmissivity of the foil 132 enables the display 24 to be clearly seen by the user when it has been activated by the control circuit 66, as shown in FIG. 10.

In use, the user first fills the fluid reservoir 34 with working fluid, which in this embodiment is water. With the closure member 102 moved to an open position to expose the fluid port 100, the user may place the appliance 10 beneath the spout of a tap and turn on the tap so that water from the spout enters the recess 142 of the handle 12. The curved wall 144 of the recess 142 guides water through the fluid port 100 and into the fluid reservoir 34. As the external wall of the fluid reservoir 34 is transparent, the user can observe the filling of the fluid reservoir 34.

To operate the appliance 10, the user presses buttons 18, 20, 22 located on the handle 12. The user switches on the appliance 10 by depressing button 18, the action of which is detected by the control circuit 66. The control circuit 66 may activate the display 24 to indicate to the user that the appliance 10 has been switched on. The user may select a mode of operation of the appliance 10 by depressing button 20. For example, through pressing button 20 once, the control circuit 66 may activate the motor to move the brush unit 29 relative to the handle 12. Pressing that button 20 again may switch off the motor. When the button 22 is pressed, a burst of water is emitted from the nozzle 36. The control circuit 66 activates the pump 48 to urge a volume of water from a fluid chamber of the pump 48 to the nozzle 36, and to replenish the fluid chamber through drawing a volume of water from the fluid reservoir 34.

The invention claimed is:

1. A dental cleaning appliance comprising:
   a handle;
   a display; and
   a control circuit for activating the display,
   wherein the handle comprises a body and a transparent panel connected to the body, the panel defining a trough-shaped recess that extends longitudinally in a longitudinal direction of the handle, and wherein the display is located beneath the recess such that the display is viewable through the recess.

2. The appliance of claim 1, wherein the recess is concave in shape.

3. The appliance of claim 1, wherein the recess is defined by a concave wall of the panel.

4. The appliance of claim 3, wherein the concave wall extends substantially the length of the recess.

5. The appliance of claim 3, wherein the body is substantially cylindrical in shape, and wherein the radius of curvature of the concave wall is smaller than the radius of curvature of the body.

6. The appliance of claim 3, wherein the panel is formed from a different material from at least an adjoining portion of the body.

7. The appliance of claim 6, wherein said at least an adjoining portion of the body is overmolded on to the panel.

8. The appliance of claim 6, wherein the body of the handle is formed from a blend of polycarbonate (PC) and acrylnitrile-butadiene-styrene (ABS) materials.

9. The appliance of claim 1, wherein the panel is formed from a transparent polycarbonate material.

10. The appliance of claim 1, wherein the handle comprises at least one user-operable button having a flexible membrane which is pressed by the user to operate the button, and wherein the flexible membrane is molded on to the panel.

11. The appliance of claim 10, wherein the flexible membrane is formed from a thermoplastic elastomeric material.

12. The appliance of claim 1, wherein the body comprises an end surface, and wherein the recess adjoins the end surface of the body.

13. The appliance of claim 1, wherein the display comprises an elongate display.

14. The appliance of claim 1, wherein the display comprises an OLED display.

15. A handle for a dental cleaning appliance, the handle being detachably connectable to a cleaning tool of the appliance, the handle comprising:
   a body;
   a transparent panel connected to the body, the panel defining a trough-shaped recess that extends longitudinally in a longitudinal direction of the handle;
   a display; and
   a control circuit for activating the display,
   wherein the display is located beneath the recess such that the display is viewable through the recess.

16. The handle of claim 15, wherein the recess is concave in shape.

17. The handle of claim 15, wherein the recess is defined by a concave wall of the panel.

18. The handle of claim 17, wherein the concave wall extends substantially the length of the recess.

19. The handle of claim 17, wherein the body is substantially cylindrical in shape, and wherein the radius of curvature of the concave wall is smaller than the radius of curvature of the body.

20. The handle of claim 17, wherein the panel is formed from a different material from at least an adjoining portion of the body.

21. The handle of claim 20, wherein said at least an adjoining portion of the body is overmolded on to the panel.

22. The handle of claim 20, wherein the body is formed from a blend of polycarbonate (PC) and acrylnitrile-butadiene-styrene (ABS) materials.

23. The handle of claim 15, wherein the panel is formed from a transparent polycarbonate material.

24. The handle of claim 15, wherein the handle comprises at least one user-operable button having a flexible membrane which is pressed by the user to operate the button, and wherein the flexible membrane is molded on to the panel.

25. The handle of claim 24, wherein the flexible membrane is formed from a thermoplastic elastomeric material.

26. The handle of claim 15, wherein the body comprises an end surface, and wherein the recess adjoins the end surface of the body.

27. The handle of claim 15, wherein the display comprises an elongate display.

28. The handle of claim 15, wherein the display comprises an OLED display.

* * * * *